United States Patent [19]

Kummer

[11] 4,437,346

[45] Mar. 20, 1984

[54] MILKMETER MEASURING THE WEIGHT OF THE QUANTITY OF MILK ISSUED BY A COW, AND DEVICE FOR TAKING SAMPLES ADAPTED FOR USE WITH SAID MILKMETER

[76] Inventor: Jan Kummer, Oostergrachtswal 91-95, 8921 AB, Leeuwarden, Netherlands

[21] Appl. No.: 319,612

[22] Filed: Nov. 9, 1981

[30] Foreign Application Priority Data

Nov. 14, 1980 [NL] Netherlands .......................... 8006246
May 13, 1981 [NL] Netherlands .......................... 8102359

[51] Int. Cl.$^3$ ............................................. G01F 11/00
[52] U.S. Cl. .................................... 73/221; 73/861.02;
73/863.57; 73/863.86; 73/198
[58] Field of Search ............. 73/221, 224, 198, 863.02,
73/863.57, 863.83, 863.86

[56] References Cited

U.S. PATENT DOCUMENTS

| 1,341,898 | 6/1920 | Gendar | 73/198 |
|---|---|---|---|
| 1,659,372 | 2/1928 | Nagel | 73/198 |
| 2,853,877 | 9/1958 | Smith | 73/224 |
| 2,882,724 | 4/1959 | Smith | 73/224 X |
| 2,917,926 | 12/1959 | Jaquith | 73/198 X |
| 4,306,454 | 12/1981 | Olrik et al. | 73/224 |

FOREIGN PATENT DOCUMENTS 261813 5/1970 U.S.S.R. ................................ 73/224

*Primary Examiner*—Herbert Goldstein
*Attorney, Agent, or Firm*—Murray Schaffer

[57] ABSTRACT

The milk weight is accurately determined by a vertical elongate float (6, 46) in the measuring container (1) cooperating with a stationary switch (10). This switch actuates the supply (3) and discharge (5) valves in the container when the float reaches its uppermost position and at the same time issues a signal to a registration counter (not shown) for the milk quantities received in the container.

The sampling device either has a sample holder (8) below the measuring container (1), comprising a sample receiving volume (11) with open upper end, or an aperture (52) in the discharge valve (49) seat (50). Thereby in operation a proportional portion of the milk quantities passing through the measuring container (1) is collected in a mixing beaker (23), from which a sample bottle (28) may be filled.

12 Claims, 11 Drawing Figures

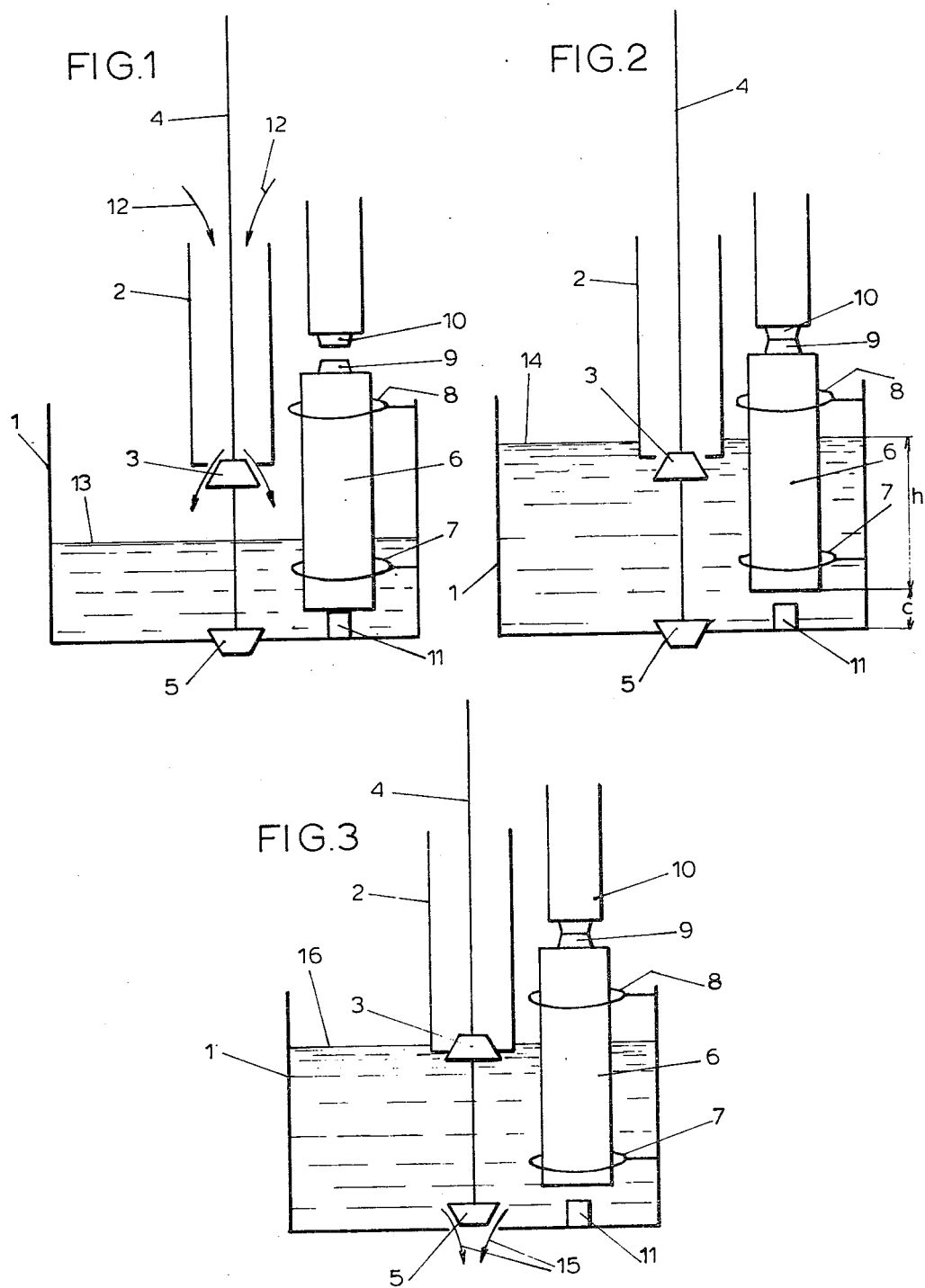

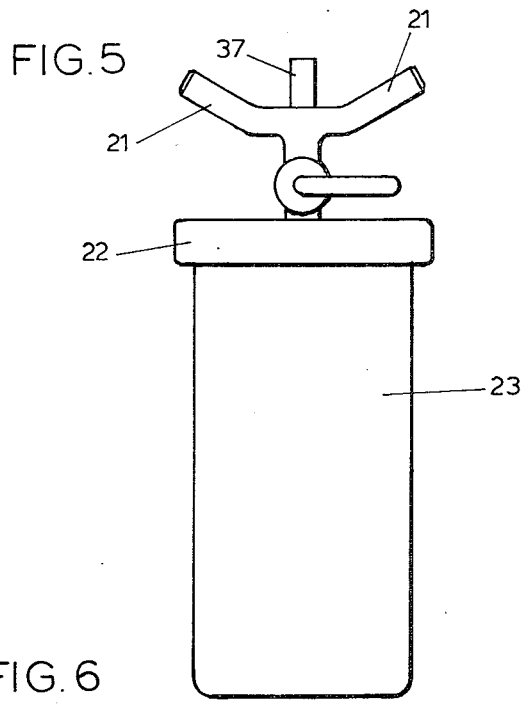
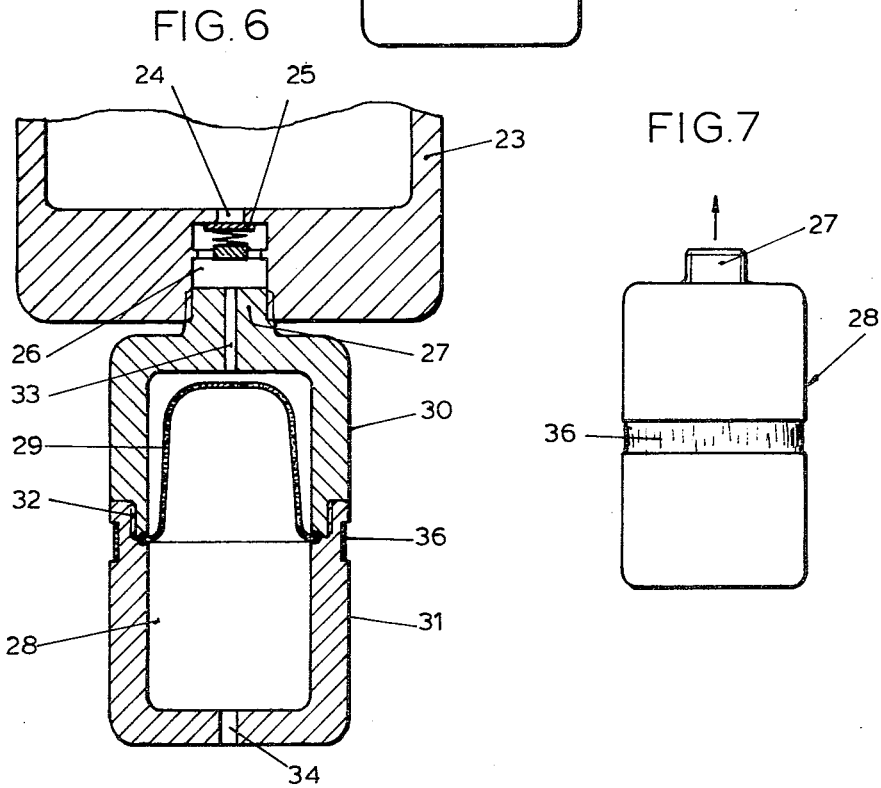

MILKMETER MEASURING THE WEIGHT OF THE QUANTITY OF MILK ISSUED BY A COW, AND DEVICE FOR TAKING SAMPLES ADAPTED FOR USE WITH SAID MILKMETER

The invention relates to a milkmeter for determining the weight of the quantity of milk issued by a cow during milking, said meter comprising a measuring container, a supply valve and a discharge valve, for supplying or discharging resp. the milk to and from the container resp.

Milkmeters measuring directly the weight of the milk are known but not accurate. They operate e.g. through a tiltable cup. Also milkmeters are known which are adapted to determine the weight indirectly through measuring of volumes. Therewith the circumstance has to be taken into account, that, due to the milking process and the flow of milk through the meter, air is absorbed into the milk, whereby the specific weight of the milk is changed relative to the stationary situation.

The invention aims at providing an accurate milkmeter of the type operating through direct measuring of the weight.

This is achieved according to the invention by a milkmeter of the type as mentioned in the beginning of this specification in that a vertically movable, guided elongate float is provided in the measuring container, the upper end of said float being adapted to cooperate with a stationary switch provided over said upper end in the measuring container, said switch closing the milk supply valve and opening the milk discharge valve if it is contacted by the upper end of the float.

Calculation shows that the height position of the float in the measuring container, e.g. relative to the position of the switch, substantially exclusively depends on the weight of the milk received in the measuring container. Independently of the specific weight of the milk, which mainly varies due to the quantity of air absorbed therein, in the fixed switching position of the float, always the same weight of milk is present in the measuring container.

The invention further comprises a device for taking samples, adapted to be used with an intermittently operating milkmeter of the above described type, comprising at least one measuring container having a milk discharge valve.

Milkmeters for measuring the quantity of milk issued by a cow are known, e.g. from the Dutch patent applications Nos. 7908184 and 8001991. Said meters operate intermittently, that is that each time after a measuring container has been filled with milk, an electric signal is issued, whereafter said measured quantity is discharged to a receiving tank, usually through a valve in the bottom of the measuring container.

It is usual to regularly take a sample of the milk of a cow for determining the fat and protein contents thereof, so that the quality of the obtained milk may be inspected.

The invention aims at providing a device for taking samples, which may be connected with one of the above mentioned intermittently operating milkmeters, so that quickly and easily samples may be taken.

This is achieved according to the invention in that a tubular holder is provided in the bottom of the milkmeter, below the milk discharge valve, part of said holder extending upwardly from the bottom, the holder having at its open end a sample receiving volume with a discharge aperture closable by a bottom valve.

Each time when the milk discharge valve of the measuring container opens, a portion of the milk flowing away from said container is received by the sample receiving volume of the tubular holder. An important portion of said milk received in the holder flows over the edge thereof and leaves the holder. A predetermined proportional portion, e.g. 1.5 cm$^3$, remains in the holder. This volume may be removed towards a sample bottle to be connected to the lower end of the holder, by opening the bottom valve of the receiving volume.

Preferably the upper edge of the sample receiving volume is extended upwardly through substantially the height of said receiving volume by a further wall portion, throughgoing apertures being provided at the transition point between said further wall portion and the upper edge. Due to the fact that the milk falls on the bottom of the receiving volume, part thereof moves upwardly along its wall and leaves the receiving volume so that the possibility exists that the volume is not completely full after the measuring container has been emptied. This is avoided by the above mentioned preferred embodiment.

It is possible to actuate the bottom valve of the receiving volume mechanically by providing the milk discharge valve of the measuring container with a downward projection when the bottom valve of the sample receiving volume is a valve, having a valve rod extending to above the upper edge or above the further wall portion resp. of the sample receiving volume. For transmitting the milk from the receiving volume of the sample holder to a sample bottle, the tubular holder is at its lower end provided with a connecting sprout, whereby a plurality of samples of the same milking may be transmitted to a mixing beaker. From that beaker a sample may be transmitted to a sample bottle.

In order to ensure that the milk samples obtained are still more accurately representative for the milk from which they are taken it would be preferable if the sample always were an accurately proportional portion of the weight contents of the measuring container.

Usually the last quantity of milk of a milking will not completely fill the measuring container. If now the sample obtained comprises a fixed quantity of milk, this quantity is no longer a proportional part thereof if the measuring container is not completely filled and therefore the milk of such a last contents of the measuring container is overrepresented in the total sample in the mixing beaker. Since said last quantity of milk of a milking, moreover, often contains a higher fat percentage than the main quantity, this results in some distortion of the fat percentage determined on the basis of the mixing beaker sample.

The still greater accuracy of the samples as here intended may be achieved by constructing the milkmeter such that in the milkmeter bottom situated below the milk discharge valve, a sampling tube has been provided extending upwardly from said bottom, the upper end of said tube being connected to a throughgoing sampling aperture in the bottom of the measuring container, said aperture being opened and closed simultaneously with the discharge valve in the bottom of the measuring container.

Although the sampling aperture may be controlled by a separate small valve, electromagnetically actuated, or by a separated small valve connected to the valve rod of the milk discharge valve, the structure is more simple if the sampling aperture in the bottom of the measuring container is provided in the seat of the discharge valve and is closed by said valve when the valve itself is closed. Preferably the connection between the sampling aperture and the upper end of the sampling tube is a channel-shaped tube, open at its upper end and extending substantially horizontally. Said tube may then be thoroughly cleaned when the milkmeter is flushed after use in that the flushing liquid meets with less resistance.

In connection with the cleaning it is likewise advantageous, as will be clear, if the discharge end of the connecting tube extends freely into the upper end of the sampling tube and if said sampling tube is provided removably in the milkmeter bottom, e.g. through a screw connection.

The structure may be further simplified if, when two measuring containers for the milk and two discharge valves for the milk are present, the connecting tubes thereof have a common discharge end towards the single sampling tube.

An advantageous embodiment of a sample bottle is obtained if in the interior wall of the bottle, at half the height thereof, an elastic membrane is secured which in its both extreme positions engages the interior of the upper and lower half resp. of the bottle, a pressure or vacuum connection aperture being provided in its bottom. Therewith the milk is not damaged during entering and removing the milk to and from the bottle resp., while only half of the bottle comes into contact with milk which enables a quicker cleaning of the bottle. Cleaning may also be done by actuating the membrane through a pressurized fluid, with the intermediary of a cleaning agent.

If it is not desired to take samples, during use of the milkmeter, the sample holder may be removed from the milkmeter if the tubular holder comprises exterior screw thread or a bayonet catch or similar means whereby the holder may be releasably connected to the bottom of the milk discharge container of the milkmeter. The aperture may then be closed by a screw or bayonet plug.

The invention further relates to an improvement of the above described milkmeter operating through measuring the weight of the milk by means of a float, said improvement being such that thereby the influence of the milk supply tube, or other parts in the measuring container changing its horizontal cross-section, is compensated.

The invention will hereunder be further illustrated with reference to the drawing, which shows a schematic embodiment of the milkmeter according to the invention.

FIG. 1 shows the meter during filling.

FIG. 2 shows the meter in the position in which the float actuates the switch.

FIG. 3 shows the meter during emptying.

FIG. 5 shows a mixing beaker.

FIG. 6 is a section through a sample bottle connected to the lower end of a mixing beaker.

FIG. 7 shows a sample bottle.

Figure 4:
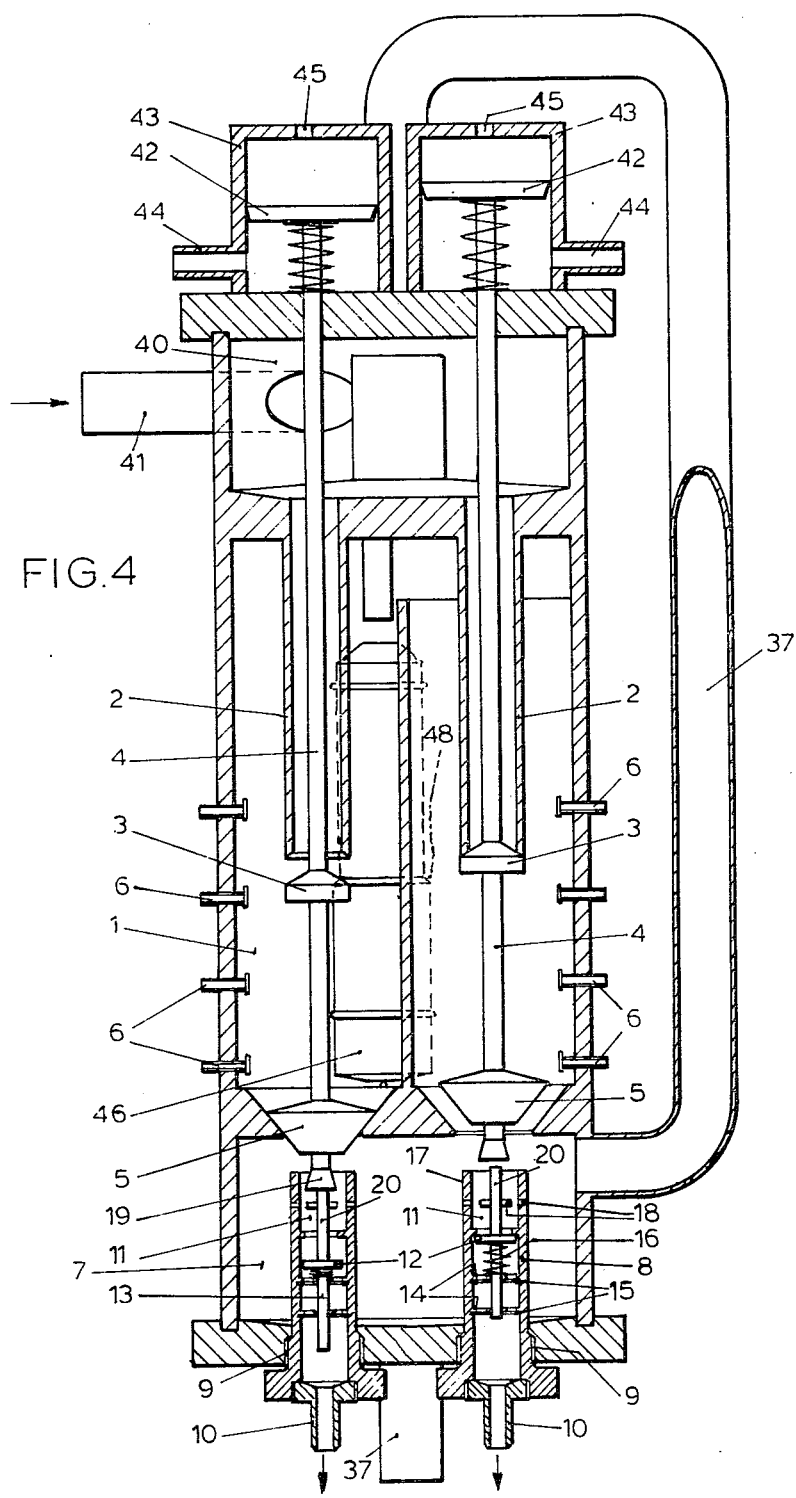
FIG. 4 is a vertical section through a milkmeter with device for taking samples.

The milkmeter as shown comprises a measuring container 1 over which a milk supply tube 2 has been provided. Said tube 2 may be closed at its lower end by a milk supply valve 3 provided on an actuating rod 4 which at its lower end, at the position of the bottom of the measuring container 1, supports a milk discharge valve 5.

An elongate float 6 is provided vertically within the measuring container 1 adjacent its wall and is vertically movable guided by guiding means, e.g. ring shaped means 7, 8 as shown, connected to the wall. On the upper end of the float 6 a magnet 9 has been provided, which is adapted to cooperate with a Hall-switch 10 secured over the float in the milkmeter. An abutment 11 may be provided on the bottom of the measuring container below the float 6, the float being supported by said abutment when the measuring container is empty.

The meter shown operates as follows: In the lower position of the float 6 as shown in FIG. 1, in which the float is supported by its abutment 11, an actuating signal has been issued by a control device not shown, to the valve rod 4, whereby said valve is moved downwardly, so that the milk supply valve 3 is open and the milk discharge valve 5 is closed. If now milk flows towards the supply tube 2 according to the arrows 12 this milk flows through the bottom of the tube 2, which has been opened by the valve 3, into the measuring container and is collected therein, since the bottom valve 5 is closed.

An arbitrary milklevel is indicated in FIG. 1 by the reference number 13. When the milk in the container 1 has attained a predetermined height, the float 6 starts floating and moves upwardly in the direction of the switch 10.

In FIG. 2 the position has been obtained in which the magnet 9 has contacted the switch 10. In that moment the milk has attained the level 14. Due to the contact with the magnet 9 the switch 10 issues a control signal, whereby the valve rod 4 moves upwardly, the supply valve 3 is closed and simultaneously the discharge valve 5 is opened. This position is shown in FIG. 3, in which likewise is shown that now the milk flows from the measuring container according to the arrows 15, while the milk level has lowered somewhat from the level according to FIG. 2 to the level 16 in FIG. 3. Apart from issuing a signal by the switch 10 for moving the valve rod 4, it likewise has issued a signal that a predetermined milkweight, e.g. 400 grams, has been received in the container 1. This signal is registered by a counter not shown and added to equal weight quantities already registered earlier.

As said, always when the float reaches its position as indicated in FIG. 2, independent of the height of the level 14, a fixed weight of milk is present in the container. The height of the level 14 namely depends on the quantity of air which has been absorbed by the milk during milking and during flowing through the milkmeter. This air leaves the milk at the top of this quantity during measuring, so that the air contents also changes as a function of the time, e.g. during filling.

The constant weight may be explained as follows: Let us assume that the float has a cross-sectional area O and that the measuring container 1 has a cross-sectional area A. As soon as the float floats on the milk, this has at any moment an immersed depth h e.g. as shown in FIG. 2.

If at the same moment the average specific weight of the milk is s then the equation is valid for the upward force on the float $K=hOs$. Since the float is floating, K is equal to G, the weight of the float.

If the level 14 in FIG. 2 in the container 1 is indicated by H then the equation is valid that the measured milk weight is $$(HA-hO)s=HAs-hOs.$$

Since the weight of the float is constant, it appears from the above that also hOs always has the same value.

If the height between the lower end of the float 6 and the bottom of the measuring container 1 is indicated c, then by the fixed position of the switch 10 the value c in the measuring position of FIG. 2 is likewise constant, so that the following equation is valid:

$$HAs=(h+c)As=hAs+cAs.$$

Since $h \times s$ is constant, likewise hAs is constant. The term cAs is not constant, however, since s is not constant. However, due to the elongate or rodlike shape of the float, which extends through substantially the complete filling height of the container 1, h is large relative to c and the term cAs is negligible with reference to hAs. Moreover, the term cAs deals with the specific weight of the milk in the lower part of the container, below the float. Since the air continuously moves upwardly in the container 1, at the moment the measuring is taken, already a large portion of the air will have left said lower part of the container, so that the specific weight of the milk there will approximate the specific weight of milk without air, e.g. substantially 4.03.

Summarizing therefore it may be said, that approximately the weight as measured by the meter is constant, independent of the quantity of air absorbed by the milk.

It will be clear that the above mentioned Hal-switch 10 may be replaced by other known switching means, such as measuring through induction, by means of a beam of light, infrared measuring, a variometer circuit, by capacity or in a different manner.

Although it has been said above that the valves 3 and 5 are provided on the same valve rod 4, this is not necessary. They may be actuable separately by the signals, also one after the other, in which e.g. first the valve 5 is closed and thereafter the valve 3 is opened.

It is preferable to have the milk supply tube 12 extend along such distance into the measuring container, that its lower end is in the milk when this reaches its uppermost level (FIG. 2). The milk surface, in which the float is floating, is then calm when the magnet 9 approaches the switch 10, so that no errors occur due to waves in the milk surface, which may occur as long as the milk falls from the end of the supply tube on said surface (FIG. 1).

The milkmeter shown in FIG. 4 has two measuring containers 1, for each of which a device for taking samples is provided. Since the arrangement is identical for both measuring containers, only one will be discussed.

A milk supply tube 2 opens into the measuring container 1 and extends downwardly from a milk supply reservoir 40 into which the milk issuing from a cow is supplied by a hose (not shown) connectable with a supply sprout 41. The lower end of the milk supply tube 2 may be closed by a milk supply valve 3, provided on a valve rod 4. The valve is actuatable through a spring loaded piston 42 contained in a cylinder 43, namely pneumatically through a vacuum connection 44 and an atmospheric air connection 45. An aperture in the bottom of the measuring container 1 has a milk discharge valve 5, provided on the same valve rod 4. When the milk supply valve 3 closes the milk supply tube 2, the milk discharge valve 5 is open (right part of FIG. 4), while when the valve 3 is open, the valve 5 closes the bottom aperture of the measuring container (left half of FIG. 4). Milk, which is supplied by the supply tube 2, flows into the measuring container 1 if the valve 3 is open.

For measuring the milk quantity the meter shown uses the principle of the meter described at the start of this specification. Therewith the weight of the milk is determined through a float. Such a float is indicated in FIG. 4 with the reference number 46. Said float is further improved relative to that according to FIGS. 1–3. Reference in this respect is made to FIG. 8. It will be clear that the measured milk quantity is no longer equal to (HA-hO)·s as soon as the milk reaches the lower end of the supply sprout 2, but is smaller corresponding to the immersed volume of said sprout. This is compensated for according to the invention, by a closed tube 47 or other prismatic body with equal cross-section as the sprout 2, which is provided in the container extending from its bottom to the lower end of the sprout 2.

Figure 9:
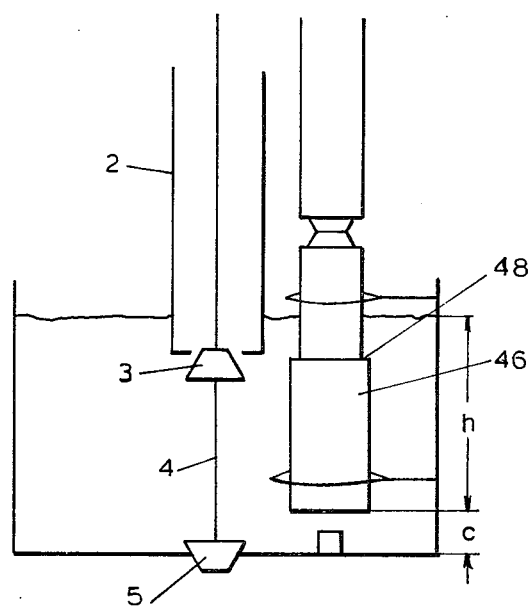
FIG. 9 shows schematically the milkmeter wth compensated float.

A different solution is indicated in FIG. 9, likewise visible in FIG. 4. Therewith the float 46 is stepped (48) i.e. having a diameter difference, such that this difference produces a difference in cross-sectional area $O_1-O_2$ corresponding to the cross-sectional area of the supply sprout 2. The step in the diameter has to be at equal height as the lower end of the sprout 2, when the float is in the measuring position corresponding to FIG. 2.

The last quantity of milk obtained from a milking usually not completely fills the measuring container 1, so that the float 2 will not be floated and does not transmit the quantity through the switch to the counter. Therefore electrodes 6 have been provided in the wall of the measuring container, regularly spaced above each other, so that if the milk reaches the level of the lower electrodes 6, the quantity of milk in the measuring container is e.g. substantially 100 grams. If thereafter the milk further rises and reaches the second electrodes 6, as seen from below upwards, then a quantity of 200 grams of milk is present in the container. When reaching the upper electrode 6 a quantity of 400 grams of milk is present in the measuring container. Each electrode is connected such with an electronic device, not shown, that when the milk reaches the electrode, it issues a signal to the counter, that again 100 grams have been measured.

When the float 46 operates its switch, the electronic device moves the valve rod 4 upwardly so that the valve 3 closes and the valve 5 is open. The quantity of milk in the measuring container now flows through the aperture in the bottom thereof, into a collecting chamber 7 of the milkmeter. From there the milk may be transported through an aperture in the bottom of this chamber to a receiving tank (not shown).

According to the invention a sample holder 8 has been provided in the bottom of the collecting chamber 7 below each measuring container 1. The holder 8 is in the embodiment shown a cylinder with open upper end, provided with exterior screw thread 9, whereby the holder may be screwed into the bottom such that its upper part extends upwardly from the bottom up to a short distance below the valve 5. The holder 8 has a discharge sprout 10 at its lower end, which is indicated here as a separate part, screwed into the bottom, in connection with easy cleaning the tubular holder.

In the upper end of the holder a sample receiving volume 11 has been formed, which is closed at its lower end by a bottom valve 12. The valve has a valve rod 13 which is guided by, in this embodiment, two guides 14, e.g. comprising an inner ring and an outer ring, said rings being mutually connected through radial webs. Each guide 14 is fixed at its position in the tube 8 by a Seeger clip 15. A compression spring 16 is enclosed between the upper guide 14 and the valve 12, said spring biasing the valve 2 to its closed position.

As indicated above, the sample receiving volume 11 is prolonged at its upper end with a further wall portion 17, throughgoing apertures 18 being provided between the wall of the volume 11 and the wall 17 whereby the milk does not reach a higher level in the upper part of the holder than the lower edge of said apertures 18.

In the milkmeter shown the valve rod 4 extends downwardly beyond the valve 5, so that a projection 19 is formed at the lower side of the valve 5. Thereby mechanical actuation of the bottom valve 12 of the sample volume is possible if also the valve rod 14 of the valve 12 is extended beyond said valve upwardly with a projection 20, which preferably ends somewhat above the upper edge of the further wall portion 17. In the milkmeter shown both discharge sprouts 10 of the sample holders may be connected through hoses with supply sprouts 21 provided on the upper cover 22 of a mixing beaker 23 (FIG. 5). The mixing beaker 23 has a volume such that therein a large number of samples may be collected. Said samples are mixed in the beaker so that the samples of the beginning of the milking are mixed with samples of the end of the milking, so that the contents of the mixing beaker indicate the average milk composition.

It appears from FIG. 5 that a discharge aperture 24 having a spring loaded valve 25 is provided in the bottom of the mixing beaker 23. The aperture 24 merges at its lower end with a wider aperture 26 into which the neck 27 of a sample bottle 28 may be inserted.

An elastic membrane 29 is secured in the interior wall of said bottle at half the height thereof, said membrane engaging in its both extreme positions with the interior of the upper and lower half resp. of the bottle. In the embodiment shown the bottle 28 comprises two parts, an upper part 30 and a lower part 31, which are screwable at 32 and simultaneously clamp the membrane 29 fixed to one of said parts. The bottle has a narrow milk supply aperture 33 in the neck 27 and an aperture 34 in the bottom of the lower part 31. A vacuum connection may be connected to said aperture 34 whereby the membrane 29 may be urged to its lower extreme position and simultaneously milk may be sucked from the mixing beaker 23 through the channel 33 into the upper chamber of the bottle. The bottle may now be disconnected from the mixing beaker and be stored. In the laboratory a pressurised air connection may be connected with the aperture 34, whereby the membrane takes its upper extreme position as indicated in FIG. 5, whereafter the milk present in the upper half of the bottle above the membrane may be entered into a test tube through the channel 33. In the outer perifery of the bottle 28 a groove 35 has been formed into which a magnetic strip 36 may be placed on which all data of the cow milked and the date of the milking may be recorded.

The operation of the device is as follows that when a measuring container 1 of the milk meter is opened through opening of the valve 5, milk flows into the collecting chamber 7. A small portion of said milk is received by the tubular holder 8 and a proportional portion thereof, equal to the sample receiving volume 11, remains therein after all milk has flowed from the measuring container 1. The remainder of the milk leaves the collecting chamber 7 through a discharge sprout 37 of the milkmeter. If now the valve 5 of one measuring container is closed and simultaneously the valve 5 of the other measuring container is opened the projection 19 of the valve rod 4 pushes the projection 20 of the valve 12 of the sample holder and the milk flows from the volume 11 through the guides 14, which let the milk pass, to the discharge sprout 10 of the holder and from there to the connected mixing beaker 23. Said mixing beaker has in the embodiment shown two connecting sprouts 21 for both measuring containers of the milkmeter of FIG. 1. Further said mixing beaker 23 has a sprout 37 communicating with the atmosphere, for discharging air from the mixing beaker, which is driven out by the entering milk.

After shaking the mixing beaker a sample bottle may be filled therefrom in the manner as described above, for laboratory tests, said bottle then containing a sample which is representative for the total milk quantity.

Figure 8:
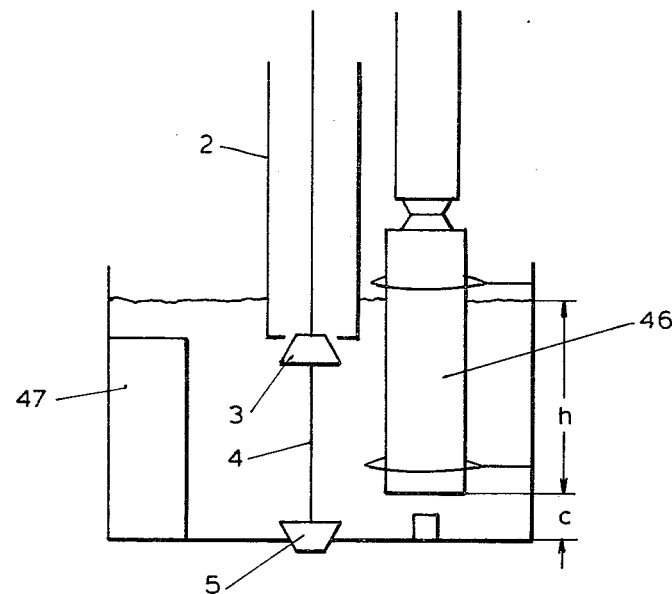
FIG. 8 shows schematically the milkmeter with float and compensating body.

It will be clear that the compensation according to FIGS. 8 and 9 may be achieved in general by ensuring that the milk containing cross-section is identical at each level. This may also be obtained through locally narrowing or widening resp. the measuring container, whereby all parts which may have been provided in the container may be compensated for.

It is to be noted that apart from compensation for equalizing the milk containing section at each level also a compensator body may be provided in order to obtain that the milk, which is present below the level of the lower end of the float 1 in the measuring position thereof is measured as milk with the average specific weight of the remainder of the measuring container contents. This body then would extend from the bottom along the height H, the maximum milk level, and has a volume=cA.

The milk discharge valves according to FIG. 1 may also have a reversed conical shape so that they close when moved downwardly and open when moved upwardly. The seat of the bottom valve 12 of the sample holder then has to be at the upper side of the valve, contrary to FIG. 1.

Figure 10:
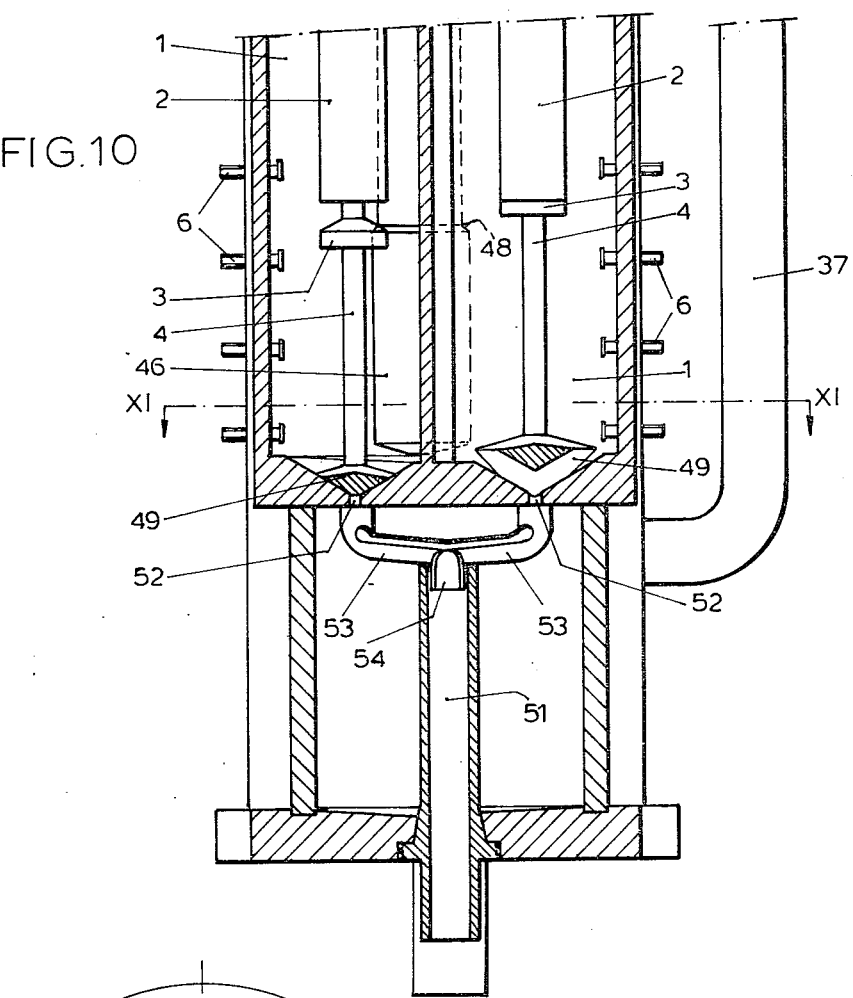
FIG. 10 shows a schematic vertical section through the lower end of a modification of the milkmeter.
Figure 11:
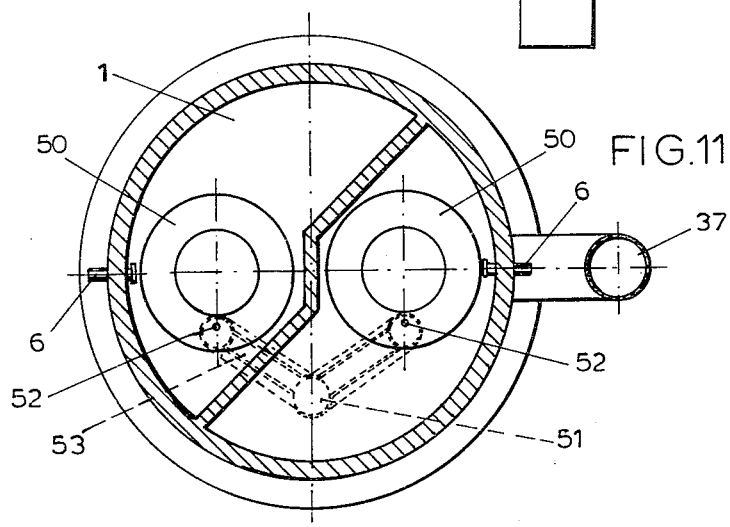
FIG. 11 is a horizontal section along VIII—VIII of FIG. 7.

In FIGS. 10 and 11 a modification of the milkmeter is shown. In this modification the sample holder 8 is replaced by the following structure.

In the seat 50 of the milk discharge valve 49 in the bottom of the measuring container 1 a throughgoing aperture 52 of small diameter is provided, the lower end of which is connectable with a connecting tube 53. Said tube at first extends vertically through a short distance, from the sampling aperture 52 and thereafter horizontally and leads to the upper end of a sampling tube 51. In the embodiment shown said tube is connected in the bottom of the milkmeter through a screw connection, a sprout extending below said bottom to which the hose from the sampling beaker may be connected. In the embodiment shown the milkmeter comprises two measuring containers 1 and therefore likewise two sampling apertures 52 and two connecting tubes 53. Said connecting tubes are joined at their discharge ends adjacent the upper end of the sampling tube 51 to an integrated structure and have a discharge sprout 54 fitting within the upper end of the tube 51. Further the tubes 53 are channel-shaped in that they are open at their upper sides. This results in advantages when cleaning the milkmeter.

Each time when the valve 49 opens, a proportional part of the milk contents of the meter 1 flows through the aperture 52 and thereby is received in the mixing beaker 23. Also when the meter is filled for only a small portion during the last milking of the cow, a proportional part thereof is received in the beaker so that said last milk quantity is not over-represented in the total milk sample.

I claim:

1. A milkmeter for intermittantly determining the weight of a quantity of milk issued by a cow during milking, comprising a measuring container, a supply valve and a discharge valve for supplying and discharging the milk to and from the container respectively, an elongated float movable freely in a vertical direction in said measuring container, in response to the level of milk therein, the upper end of said float being provided with a means which cooperates with switch means mounted in a stationary position in opposition to said float over the upper end of the measuring container, said switch acting to close the milk supply valve and to open the milk discharge valve when contacted by the upper end of the float, the distance between the lower end of said float and the maximum milk level in said measuring container when said float is contacted with the switch, being large relative to the spacing of the lower end of said float from the bottom of said measuring container.

2. The milkmeter according to claim 1 wherein said switch means comprises an electrical switch activated by magnetic means, and said float is provided with a magnet at its upper end.

3. The milkmeter according to claim 2 including a collecting chamber mounted below said measuring container for receiving the milk discharged through the discharge valve, an outlet from said collecting chamber and valve means operable on closing of said discharge valve to open said outlet for delivering of milk therefrom.

4. The milkmeter according to claim 3, including a tubular holder extending through said collecting chamber in opposition to said discharge valve, a plurality of holes located in the wall of said tubular holder adjacent the upper end thereof, an aperture valve seat located axially in said tubular holder below said holes, a closure member adapted engage said valve seat, said closure member having a valve rod extending upwardly through said tubular holder in opposition to said milk discharge valve, and spring means normally biasing said closure member against said seat, said closure member being opened on closure of said discharge valve, wherein the tubular holder is provided at its lower end with a connecting spout.

5. The milkmeter according to claim 3 including a sampling tube located below the milk discharge valve, the upper end of said sampling tube being connected to a sampling aperture in the seat of the milk discharge valve, and being opened and closed respectively simultaneously with the discharge valve.

6. The milkmeter according to claim 5 wherein the sampling aperture and the upper end of the sampling tube is a channel-shaped connecting tube, which is open along its upper side and extends substantially horizontally.

7. The milkmeter according to claim 6 wherein the discharge end of the connecting tube extends freely into the upper end of the sampling tube and screw means is provided for removably connecting said sampling tube to the bottom of said collecting chamber.

8. The milkmeter according to claim 6 having two milk measuring containers each having a milk discharge valve, and connecting tubes forming a common outlet.

9. The milkmeter according to claim 2, wherein said measuring container is selectively shaped in cross section along its length such that the milk containing horizontal section of the measuring container is equal at each level of said float.

10. The milkmeter according to claim 2 including means provided along the maximum filling height of the measuring container compensating for the volume of the portion of said container below the float when said float is in its upper most position.

11. The milkmeter according to claim 3, wherein the tubular holder is provided with means for releaseably connecting said tubular holder to the collecting chamber.

12. The milkmeter according to claim 1, including a bottle adapted to be connected to said tubular holder having an opening for receiving milk therein, an elastic membrane secured in the interior wall of the bottle at half its height, said membrane engaging in its both extreme positions with the interior of one of the upper and lower half respectfully of the bottle, and an aperture in the bottom of said bottle for connection to a pressure or vacuum source.

* * * * *